US012778777B2

(12) United States Patent
Bagaoisan et al.

(10) Patent No.: US 12,778,777 B2
(45) **Date of Patent: *Nov. 3, 2026**

(54) VASCULAR ACCESS DEVICES AND METHODS FOR LOWER LIMB INTERVENTIONS

(71) Applicant: RAM MEDICAL INNOVATIONS LLC, Springfield, OH (US)

(72) Inventors: Celso Bagaoisan, Union City, CA (US); Suresh Pai, Los Altos, CA (US); Azim Shaikh, Beavercreek, OH (US); Mubin I. Syed, Springfield, OH (US)

(73) Assignee: RAM Medical Innovations, Inc., Springfield, OH (US)

( * ) Notice: Subject to any disclaimer, the term of this patent is extended or adjusted under 35 U.S.C. 154(b) by 59 days.

This patent is subject to a terminal disclaimer.

(21) Appl. No.: 18/974,565

(22) Filed: Dec. 9, 2024

(65) Prior Publication Data

US 2025/0099277 A1 Mar. 27, 2025

Related U.S. Application Data

(63) Continuation of application No. 18/585,026, filed on Feb. 22, 2024, now Pat. No. 12,201,541, which is a (Continued)

(51) Int. Cl.

| | |
|---|---|
| ***A61F 2/954*** | (2013.01) |
| ***A61B 17/00*** | (2006.01) |

(Continued)

(52) U.S. Cl.
CPC ........ *A61F 2/954* (2013.01); *A61B 17/32056* (2013.01); *A61F 2/966* (2013.01);
(Continued)

(58) Field of Classification Search
CPC .... A61B 17/32056; A61B 2017/00358; A61B 2017/2212; A61F 2/954; A61F 2/966;
(Continued)

(56) References Cited

U.S. PATENT DOCUMENTS

| | | |
|---|---|---|
| 3,896,815 A | 7/1975 | Fettel |
| 4,243,040 A | 1/1981 | Beecher |

(Continued)

FOREIGN PATENT DOCUMENTS

| | | |
|---|---|---|
| CN | 108472124 | 8/2018 |
| CN | 108472472 | 8/2018 |

(Continued)

OTHER PUBLICATIONS

International Search Report and Written Opinion for PCT/US2013/071271 dated Feb. 10, 2014, 7 pages.

(Continued)

*Primary Examiner* — Jocelin C Tanner
(74) *Attorney, Agent, or Firm* — Nixon Peabody LLP

(57) ABSTRACT

A guide sheath device with an integrated stabilization wire is provided. The guide sheath device includes an elongate member having a proximal and distal end and a lumen there between and a stabilization wire integrated to the elongate member.

12 Claims, 9 Drawing Sheets

Related U.S. Application Data continuation of application No. 17/202,155, filed on Mar. 15, 2021, now Pat. No. 12,011,379, which is a continuation of application No. 16/183,150, filed on Nov. 7, 2018, now Pat. No. 11,007,075.

(60) Provisional application No. 62/631,904, filed on Feb. 18, 2018.

(51) Int. Cl.

| | |
|---|---|
| ***A61B 17/221*** | (2006.01) |
| ***A61B 17/3205*** | (2006.01) |
| ***A61F 2/966*** | (2013.01) |
| ***A61M 25/01*** | (2006.01) |
| ***A61M 25/06*** | (2006.01) |
| ***A61M 25/10*** | (2013.01) |

(52) U.S. Cl.

CPC .... *A61M 25/0102* (2013.01); *A61M 25/0108* (2013.01); *A61M 25/1002* (2013.01); *A61B 2017/00358* (2013.01); *A61B 2017/2212* (2013.01); *A61M 2025/0177* (2013.01); *A61M 2025/0681* (2013.01)

(58) Field of Classification Search

CPC .............. A61M 25/0082; A61M 25/01; A61M 25/0108; A61M 25/1002; A61M 2025/0096; A61M 2025/0177; A61M 2025/0681

USPC .......................................................... 606/200

See application file for complete search history.

(56) References Cited

U.S. PATENT DOCUMENTS

| | | | | |
|---|---|---|---|---|
| 4,790,331 | A | 12/1988 | Okada et al. | |
| 5,098,707 | A | 3/1992 | Baldwin et al. | |
| 5,293,772 | A | 3/1994 | Carr, Jr. | |
| 5,344,426 | A | 9/1994 | Lau et al. | |
| 5,413,558 | A * | 5/1995 | Paradis | A61M 60/531 604/509 |
| 5,419,777 | A | 5/1995 | Hofling | |
| 5,433,705 | A | 7/1995 | Giebel et al. | |
| 5,571,135 | A | 11/1996 | Fraser et al. | |
| 5,651,366 | A | 7/1997 | Liang et al. | |
| 5,662,703 | A | 9/1997 | Yurek et al. | |
| 5,669,924 | A | 9/1997 | Shaknovich | |
| 5,690,644 | A | 11/1997 | Yurek et al. | |
| 5,718,702 | A | 2/1998 | Edwards | |
| 5,720,735 | A | 2/1998 | Dorros | |
| 5,766,192 | A | 6/1998 | Zacca | |
| 5,807,330 | A | 9/1998 | Teitelbaum | |
| 5,813,976 | A | 9/1998 | Filipi et al. | |
| 5,824,055 | A | 10/1998 | Spiridigliozzi | |
| 5,957,901 | A | 9/1999 | Mottola et al. | |
| 5,997,563 | A | 12/1999 | Kretzers | |
| 6,027,462 | A | 2/2000 | Greene et al. | |
| 6,059,813 | A | 5/2000 | Vrba et al. | |
| 6,070,589 | A | 6/2000 | Keith et al. | |
| 6,152,141 | A | 11/2000 | Stevens et al. | |
| 6,238,410 | B1 | 5/2001 | Vrba et al. | |
| 6,245,017 | B1 | 6/2001 | Hashimoto | |
| 6,245,573 | B1 | 6/2001 | Spillert | |
| 6,428,567 | B2 | 8/2002 | Wilson et al. | |
| 6,450,964 | B1 | 9/2002 | Webler | |
| 6,464,665 | B1 | 10/2002 | Heuser | |
| 6,494,875 | B1 | 12/2002 | Mauch | |
| 6,544,278 | B1 | 4/2003 | Vrba et al. | |
| 6,652,556 | B1 | 11/2003 | Vantassel | |
| 6,663,613 | B1 | 12/2003 | Lewis et al. | |
| 6,764,505 | B1 | 7/2004 | Hossainy et al. | |
| 6,780,174 | B2 | 8/2004 | Mauch | |
| 6,808,520 | B1 | 10/2004 | Fouirkas et al. | |
| 6,837,881 | B1 | 1/2005 | Barbut | |
| 6,929,633 | B2 | 8/2005 | Evans et al. | |
| 6,932,829 | B2 | 8/2005 | Majercak | |
| 6,942,682 | B2 | 9/2005 | Vrba et al. | |
| 7,235,083 | B1 | 6/2007 | Perez et al. | |
| 7,393,358 | B2 | 7/2008 | Malewicz | |
| 7,651,520 | B2 | 1/2010 | Fischell et al. | |
| 7,674,493 | B2 | 3/2010 | Hossainy et al. | |
| 7,740,791 | B2 | 6/2010 | Kleine et al. | |
| 7,758,624 | B2 | 7/2010 | Dorn et al. | |
| 7,763,010 | B2 | 7/2010 | Evans et al. | |
| 7,766,961 | B2 | 8/2010 | Patel et al. | |
| 7,828,832 | B2 | 11/2010 | Belluche et al. | |
| 7,842,026 | B2 | 11/2010 | Cahill et al. | |
| 7,955,370 | B2 | 6/2011 | Gunderson | |
| 8,092,509 | B2 | 1/2012 | Dorn et al. | |
| 8,119,184 | B2 | 2/2012 | Hossainy et al. | |
| 8,202,309 | B2 | 6/2012 | Styrc | |
| 8,241,241 | B2 | 8/2012 | Evans et al. | |
| 8,343,181 | B2 | 1/2013 | Duffy et al. | |
| 8,419,767 | B2 | 4/2013 | Al-Qbandi et al. | |
| 8,535,290 | B2 | 9/2013 | Evans et al. | |
| 8,721,714 | B2 | 5/2014 | Kelley | |
| 8,727,988 | B2 | 5/2014 | Flaherty et al. | |
| 8,728,144 | B2 | 5/2014 | Fearnot | |
| 8,740,971 | B2 | 6/2014 | Iannelli | |
| 8,986,241 | B2 | 3/2015 | Evans et al. | |
| 8,998,894 | B2 | 4/2015 | Mauch et al. | |
| 9,301,830 | B2 | 4/2016 | Heuser et al. | |
| 9,314,499 | B2 | 4/2016 | Wang et al. | |
| 9,414,824 | B2 | 8/2016 | Fortson | |
| 9,636,244 | B2 | 5/2017 | Syed | |
| 9,855,705 | B2 | 1/2018 | Wang et al. | |
| 9,980,838 | B2 | 5/2018 | Syed | |
| 10,492,936 | B2 | 12/2019 | Syed | |
| 10,779,976 | B2 | 9/2020 | Syed | |
| 10,857,014 | B2 | 12/2020 | Syed | |
| 10,888,445 | B2 | 1/2021 | Syed | |
| 11,007,075 | B2 | 5/2021 | Bagoaisan | |
| 11,020,256 | B2 | 6/2021 | Syed | |
| 12,121,674 | B2 | 10/2024 | Syed | |
| 12,201,541 | B2 * | 1/2025 | Bagaoisan | A61M 25/01 |
| 2001/0003985 | A1 | 6/2001 | Lafontaine et al. | |
| 2001/0049534 | A1 | 12/2001 | Lachat | |
| 2002/0077691 | A1 | 6/2002 | Nachtigall | |
| 2002/0123698 | A1 | 9/2002 | Garibotto et al. | |
| 2002/0156518 | A1 | 10/2002 | Tehrani | |
| 2002/0165535 | A1 | 11/2002 | Lesh | |
| 2003/0088187 | A1 | 5/2003 | Saadat et al. | |
| 2003/0204171 | A1 | 10/2003 | Kucharczyk | |
| 2003/0216721 | A1 | 11/2003 | Diederich | |
| 2003/0229282 | A1 | 12/2003 | Burdette | |
| 2004/0002714 | A1 | 1/2004 | Weiss | |
| 2004/0073190 | A1 | 4/2004 | Deem et al. | |
| 2004/0138734 | A1 | 7/2004 | Chobotov et al. | |
| 2004/0147837 | A1 | 7/2004 | Macaulay et al. | |
| 2005/0043779 | A1 | 2/2005 | Wilson | |
| 2005/0101968 | A1 | 5/2005 | Dadourian | |
| 2005/0113798 | A1 | 5/2005 | Slater | |
| 2005/0113862 | A1 | 5/2005 | Besselink et al. | |
| 2005/0222488 | A1 | 10/2005 | Chang et al. | |
| 2005/0234499 | A1 | 10/2005 | Olson et al. | |
| 2005/0251160 | A1 | 11/2005 | Saadat et al. | |
| 2005/0267010 | A1 | 12/2005 | Goodson et al. | |
| 2006/0025752 | A1 | 2/2006 | Broaddus et al. | |
| 2006/0025844 | A1 | 2/2006 | Majercak et al. | |
| 2006/0030923 | A1 | 2/2006 | Gunderson | |
| 2006/0074484 | A1 | 4/2006 | Huber | |
| 2006/0155363 | A1 | 7/2006 | Laduca et al. | |
| 2006/0200221 | A1 | 9/2006 | Malewicz | |
| 2006/0257389 | A1 | 11/2006 | Binford | |
| 2006/0259063 | A1 | 11/2006 | Bates et al. | |
| 2006/0270900 | A1 | 11/2006 | Chin et al. | |
| 2007/0016019 | A1 | 1/2007 | Salgo | |
| 2007/0016062 | A1 | 1/2007 | Park | |
| 2007/0038061 | A1 | 2/2007 | Huennekens et al. | |
| 2007/0038293 | A1 | 2/2007 | St. Goar et al. | |
| 2007/0049867 | A1 | 3/2007 | Shindelman | |
| 2007/0083215 | A1 | 4/2007 | Hamer et al. | |

(56) References Cited

U.S. PATENT DOCUMENTS

| | | | |
|---|---|---|---|
| 2007/0118151 | A1 | 5/2007 | Davidson et al. |
| 2007/0129719 | A1 | 6/2007 | Kendale et al. |
| 2007/0219614 | A1 | 9/2007 | Hartley et al. |
| 2007/0288082 | A1 | 12/2007 | Williams |
| 2008/0009829 | A1 | 1/2008 | Ta |
| 2008/0039746 | A1 | 2/2008 | Hissong et al. |
| 2008/0114239 | A1 | 5/2008 | Randall et al. |
| 2008/0194993 | A1 | 8/2008 | McLaren et al. |
| 2008/0208309 | A1 | 8/2008 | Saeed |
| 2008/0281398 | A1 | 11/2008 | Koss |
| 2008/0306467 | A1 | 12/2008 | Reydel |
| 2009/0005679 | A1 | 1/2009 | Dala-Krishna |
| 2009/0018526 | A1 | 1/2009 | Power et al. |
| 2009/0036780 | A1 | 2/2009 | Abraham |
| 2009/0132019 | A1 | 5/2009 | Duffy et al. |
| 2009/0171293 | A1 | 7/2009 | Yang et al. |
| 2009/0177035 | A1 | 7/2009 | Chin |
| 2009/0240253 | A1 | 9/2009 | Murray |
| 2009/0254116 | A1 | 10/2009 | Rosenschein et al. |
| 2009/0270975 | A1 | 10/2009 | Giofford, III et al. |
| 2009/0319017 | A1 | 12/2009 | Berez et al. |
| 2010/0016943 | A1 | 1/2010 | Chobotov |
| 2010/0024818 | A1 | 2/2010 | Stenzler et al. |
| 2010/0030165 | A1 | 2/2010 | Takagi et al. |
| 2010/0030256 | A1 | 2/2010 | Dubrul et al. |
| 2010/0069852 | A1 | 3/2010 | Kelley |
| 2010/0168583 | A1 | 7/2010 | Dausch et al. |
| 2010/0185161 | A1 | 7/2010 | Pellegrino et al. |
| 2010/0185231 | A1 | 7/2010 | Lashinski |
| 2010/0204708 | A1 | 8/2010 | Sharma |
| 2010/0211095 | A1 | 8/2010 | Carpenter |
| 2010/0268067 | A1 | 10/2010 | Razzaque et al. |
| 2010/0272740 | A1 | 10/2010 | Vertegel et al. |
| 2010/0298922 | A1 | 11/2010 | Thornton et al. |
| 2011/0009943 | A1 | 1/2011 | Paul et al. |
| 2011/0034987 | A1 | 2/2011 | Kennedy |
| 2011/0071394 | A1 | 3/2011 | Fedinec |
| 2011/0082533 | A1 | 4/2011 | Vardi et al. |
| 2011/0098681 | A1 | 4/2011 | Djurivic |
| 2011/0196420 | A1 | 8/2011 | Ebner |
| 2011/0224773 | A1 | 9/2011 | Gifford et al. |
| 2011/0230830 | A1 | 9/2011 | Gifford, III et al. |
| 2011/0270375 | A1 | 11/2011 | Hartley et al. |
| 2011/0282427 | A1 | 11/2011 | Bourang et al. |
| 2012/0016343 | A1 | 1/2012 | Gill |
| 2012/0016454 | A1 | 1/2012 | Jantzen et al. |
| 2012/0020942 | A1 | 1/2012 | Hall et al. |
| 2012/0022636 | A1 | 1/2012 | Chobotov |
| 2012/0029478 | A1 | 2/2012 | Kurosawa |
| 2012/0034205 | A1 | 2/2012 | Alkon |
| 2012/0035590 | A1 | 2/2012 | Whiting et al. |
| 2012/0046690 | A1 | 2/2012 | Blom |
| 2012/0169712 | A1 | 7/2012 | Hill et al. |
| 2012/0209375 | A1 | 8/2012 | Madrid et al. |
| 2012/0221094 | A1 | 8/2012 | Cunningham |
| 2012/0289945 | A1 | 11/2012 | Segermark |
| 2013/0053792 | A1 | 2/2013 | Fischell et al. |
| 2013/0131777 | A1 | 5/2013 | Hartley et al. |
| 2013/0218201 | A1 | 8/2013 | Obermiller |
| 2013/0296773 | A1 | 11/2013 | Feng et al. |
| 2013/0310823 | A1 | 11/2013 | Gelfand et al. |
| 2013/0331819 | A1 | 12/2013 | Rosenman et al. |
| 2013/0331921 | A1 | 12/2013 | Roubin |
| 2014/0031925 | A1 | 1/2014 | Garrison et al. |
| 2014/0114346 | A1 | 4/2014 | Mccaffrey |
| 2014/0142427 | A1 | 5/2014 | Petroff |
| 2014/0214002 | A1 | 7/2014 | Lieber et al. |
| 2014/0228808 | A1 | 8/2014 | Webster et al. |
| 2014/0276602 | A1 | 9/2014 | Bonnette |
| 2014/0358123 | A1 | 12/2014 | Ueda et al. |
| 2015/0018942 | A1 | 1/2015 | Hung et al. |
| 2015/0174377 | A1 | 6/2015 | Syed |
| 2015/0190576 | A1 | 7/2015 | Lee et al. |
| 2015/0201900 | A1 | 7/2015 | Syed |
| 2015/0245933 | A1 | 9/2015 | Syed |
| 2015/0352331 | A1 | 12/2015 | Helm, Jr. |
| 2015/0366536 | A1 | 12/2015 | Courtney et al. |
| 2015/0374261 | A1 | 12/2015 | Grunwald |
| 2016/0008058 | A1 | 1/2016 | Hu et al. |
| 2016/0038724 | A1 | 2/2016 | Madsen et al. |
| 2016/0120509 | A1 | 5/2016 | Syed |
| 2016/0120673 | A1 | 5/2016 | Siegel et al. |
| 2016/0135974 | A1* | 5/2016 | Jensen .................... A61F 2/966 623/1.11 |
| 2016/0296355 | A1 | 10/2016 | Syed |
| 2016/0338835 | A1 | 11/2016 | Van Bladel et al. |
| 2017/0119562 | A1 | 5/2017 | Syed |
| 2017/0119563 | A1 | 5/2017 | Syed |
| 2017/0135833 | A1 | 5/2017 | Syed |
| 2017/0181876 | A1 | 6/2017 | Syed |
| 2017/0304095 | A1 | 10/2017 | Syed |
| 2017/0347926 | A1* | 12/2017 | Farooqui ................ A61B 5/742 |
| 2017/0361062 | A1 | 12/2017 | Syed |
| 2018/0042743 | A1 | 2/2018 | Syed |
| 2018/0059124 | A1 | 3/2018 | Syed |
| 2018/0116780 | A1 | 5/2018 | Laine |
| 2018/0250147 | A1 | 9/2018 | Syed |
| 2019/0091441 | A1 | 3/2019 | Syed |
| 2019/0336114 | A1 | 11/2019 | Syed |
| 2020/0038210 | A1 | 2/2020 | Syed |
| 2021/0196492 | A1 | 7/2021 | Bagaoisan |
| 2022/0152347 | A1 | 5/2022 | Syed |
| 2024/0074883 | A1 | 3/2024 | Syed |
| 2024/0189127 | A1 | 6/2024 | Syed |

FOREIGN PATENT DOCUMENTS

| | | |
|---|---|---|
| CN | 108882975 | 11/2018 |
| CN | 109475722 | 3/2019 |
| CN | 111629696 | 9/2020 |
| EP | 3280355 | 2/2018 |
| EP | 3367969 | 9/2018 |
| EP | 3368123 | 9/2018 |
| EP | 3399944 | 11/2018 |
| EP | 3405261 | 11/2018 |
| EP | 3471815 | 4/2019 |
| IN | 201827018555 | 10/2018 |
| IN | 201827018768 | 10/2018 |
| WO | WO 1996/036269 | 11/1996 |
| WO | WO 1999/40849 | 8/1999 |
| WO | WO 2004/089249 | 10/2004 |
| WO | WO 2010/129193 | 11/2010 |
| WO | WO 2011/011539 | 1/2011 |
| WO | WO 2011/106502 | 9/2011 |
| WO | WO 2011/137336 | 11/2011 |
| WO | WO 2012/030101 | 8/2012 |
| WO | WO 2014/081947 | 5/2014 |
| WO | WO 2014/197839 | 12/2014 |
| WO | WO 2016164215 | 10/2016 |
| WO | WO 2017/074492 | 5/2017 |
| WO | WO 2017/074536 | 5/2017 |
| WO | WO 2017/127127 | 7/2017 |
| WO | WO 2017/222571 | 12/2017 |
| WO | WO 2017/222612 | 12/2017 |
| WO | WO 2018/164766 | 9/2018 |
| WO | WO 2019/070349 | 4/2019 |

OTHER PUBLICATIONS

International Search Report and Written Opinion for PCT/US2016/024794 dated Jul. 1, 2016, 10 pages.

International Search Report and Written Opinion for PCT/US2016/024795 dated Aug. 30, 2016, 14 pages.

International Search Report and Written Opinion for PCT/US2016/047163 dated Oct. 28, 2016, 9 pages.

International Search Report and Written Opinion for PCT/US2016/047165 dated Jan. 5, 2017, 13 pages.

International Search Report and Written Opinion for PCT/US2017/021188 dated May 10, 2017, 11 pages.

International Search Report and Written Opinion for PCT/US2018/012834 dated Mar. 15, 2018,13 pages.

International Search Report and Written Opinion for PCT/US2018/047372 dated Jan. 2, 2019, 8 pages.

(56) References Cited

OTHER PUBLICATIONS

International Search Report and Written Opinion for PCT/US2019/012727 dated Mar. 21, 2019, 12 pages.
International Search Report and Written Opinion for PCT/US2019/12745 dated Apr. 1, 2019, 10 pages.
International Preliminary Report on Patentability for PCT/US2013/071271 dated May 26, 2015, 6 pages.
International Preliminary Report on Patentability for PCT/US2016/024795 dated May 1, 2018, 10 pages.
International Preliminary Report on Patentability for PCT/US2016/047165 dated May 1, 2018, 5 pages.
International Preliminary Report on Patentability for PCT/US2017/021188 dated Dec. 25, 2018, 9 pages.
International Preliminary Report on Patentability for PCT/US2016/047163 dated Dec. 25, 2018, 7 pages.
EP 16777055.1 Extended Search Report dated Feb. 12, 2019, 7 pages.
EP 18725097.2 Extended Search Report dated Apr. 24, 2019, 9 pages.
EP 16860437.9 Extended Search Report dated May 17, 2019.
EP 16906475.5 Extended Search Report dated Jan. 24, 2020.
EP 17815838.2 Extended Search Report dated Jan. 20, 2020.
Beckman et al., Venous Thromboembolism: A Public Health Concern, Am J Prev Med., 2010, vol. 38(4), pp. S495-S501.
Blaney et al., Alteplase for the Treatment of Central Venous Catheter Occlusion in Children: Results of a Prospective, Open-Label, Single-Arm Study (The Cathflo Activase Pediatric Study), J Vasc Interv Radiol, 2006, vol. 17(11), pp. 1745-1751.
Godwin, J., The Circulatory and Respiratory Systems, Z0250 Lab III, 2002, retrieved from: https://projects.ncsu.edu/cals/course/zo250/lab-3.html.
Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.
Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.
Shah, T., Radiopaque Polymer Formulations for Medical Devices, MDDI Medical Diagnostic and Device Industry: Materials, 2001, retrieved from: https://www.mddionline.com/radiopaque-polymer-formulations-medical-devices.
Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.
Stroke Treatments, American Heart Association, Retrieved from: http://www.strokeassociation.org/STROKEORG/AboutStroke/Treatment/Stroke-Treatments_UCM_310892_Article.jsp#V9Hrg2WfV_1 on Sep. 8, 2016.
Office Action in U.S. Appl. No. 18/386,577, mailed Apr. 30, 2026 (12 pages).

* cited by examiner

VASCULAR ACCESS DEVICES AND METHODS FOR LOWER LIMB INTERVENTIONS

CROSS REFERENCE TO RELATED APPLICATIONS

This application is a continuation application of U.S. patent application Ser. No. 18/585,026, filed Feb. 22, 2024, entitled "VASCULAR ACCESS DEVICES AND METHODS FOR LOWER LIMB INTERVENTIONS", which is a continuation of U.S. patent application Ser. No. 17/202,155, filed Mar. 15, 2021, entitled "VASCULAR ACCESS DEVICES AND METHODS FOR LOWER LIMB INTERVENTIONS", which is a continuation of U.S. patent application Ser. No. 16/183,150, filed Nov. 7, 2018, entitled "VASCULAR ACCESS DEVICES AND METHODS FOR LOWER LIMB INTERVENTIONS", which claims priority under 35 U.S.C. § 119 to U.S. Provisional Application No. 62/631,904, entitled "MODIFIED FIXED FLAT WIRE BIFURCATED CATHETER AND ITS APPLICATION IN AORTO BIFEMORAL BYPASS," and filed on Feb. 18, 2018. The contents of those applications are hereby incorporated by reference in their entirety.

TECHNICAL FIELD

The present disclosure relates to improved methods and apparatuses implemented in endovascular procedures involving tortuous vasculature. Specifically, the present disclosure relates to vascular access devices and methods for accessing angulated and tortuous aortic bifurcations, tortuous lower extremity vessels and supporting the pushability of endovascular tools.

BACKGROUND

Stenting and balloon angioplasty of arteries are considered to be well characterized interventional procedures. Typically, stent placement and balloon angioplasty are performed to re-establish or normalize blood flow within the artery that may have been constricted by plaque or embolic deposits. In such procedures, vascular access in the lower extremities is often performed via a retrograde, antegrade or transpedal approach.

Antegrade access is an industry standard as it provides superior support when advancing interventional devices through relatively-straight blood vessels. However, the antegrade access procedure can be technically demanding and typically presents significant challenges in obese patients where the femoral artery may be difficult to locate in the patient's soft tissue. Furthermore, antegrade punctures that occur during the antegrade access procedure can also elicit complications (e.g. hematoma, pseudo aneurysm, hemorrhage) related to closure of the puncture site at the femoral artery access point.

The retrograde contralateral approach is the most common technique for accessing the lower limbs where an access point at the femoral artery located on one side of the body (i.e. the contralateral side) is used to access the blood vessels and lesions in the other leg on the ipsilateral side. This retrograde access is technically simple in most patients and feasible for all interventionalists. However, the retrograde procedure may present challenges when accessing the vasculature and anatomies targeted for treatment based on the anatomical disposition of the access location. For example, vascular access in a hostile anatomy with tortuous peripheral vessels and intervention of distal most blood vessels (e.g. in the popliteal and tibial arteries) can be challenging or impossible, for example, in highly tortuous vessels containing calcific plaques and/or in highly angulated aortic bifurcations.

The transpedal access procedure is a relatively new approach wherein support catheters and guidewires leverage the enhanced support provided by access of blood vessels from the foot. The pedal artery typically used for access is small and existing interventional tools are not optimally sized. This is a significant drawback because irreversible damage to tenuous blood vessels in the foot can further exacerbate the condition of patients with critical limb ischemia.

Although endovascular devices (e.g. stent delivery systems, angioplasty balloons, atherectomy devices, thrombectomy devices, etc.) are generally designed to accommodate very acute bends and tortuous anatomies in the lower extremities, these devices rely on the use of rigid guide catheters, guide sheaths and guide wires to be delivered to the target treatment site(s). When long delivery systems or other catheters are used, the performance characteristics (i.e. pushability) of these catheters and the support provided by the guide catheters, guide sheaths and guide wires become critical. As a result, guide catheters, guide sheaths and guide wires of adequate rigidity and structure are needed to most effectively manipulate these interventional devices in tortuous anatomies. Often times, tortuous arteries and access vessels can be injured during the insertion, manipulation and stabilization of the interventional tools being used during the procedure using the rigid guide catheters, guide sheaths and guide wires. Injuries can be caused by perforation or dissection of the arterial wall by the stiff guide catheters, guide sheaths and guide wires, often resulting in hemorrhage, thrombus formation leading to infarcts or even death.

Thus, there exists a need for improved methods and apparatuses that can be easily positioned and subsequently provide superior support and stability to the interventional devices to be used in a procedure thereby reducing injuries and trauma caused to the arterial walls during vascular access, and allowing faster navigation and access through difficult anatomy.

SUMMARY

A guide sheath apparatus configured to perform endovascular procedures is disclosed herein. The apparatus includes an elongate member with a proximal and distal end and a lumen there between. In some embodiments, the lumen is capable of allowing passage of guide wires. The apparatus also includes a stabilization wire integrated within the elongate member. In some embodiments, the stabilization wire extends beyond the distal tip of the elongate member. The stabilization wire can include either a round or flat material. The stabilization wire can bifurcate away from the surface of the elongate member.

The apparatus can also include a removable dilator having an elongate member with proximal and distal end and a lumen there-between. In some embodiments, the apparatus can include a tool configured to anchor the stabilization wire in place.

The elongate member can include at least one radiopaque marker. In some embodiments, a transition point of bifurcation is located between the proximal and distal end of the elongate member. The transition point of bifurcation can include a radiopaque marker. In some embodiments, the elongate member includes a radiopaque filler.

A method for performing an endovascular procedure is also provided. The method includes obtaining bilateral, percutaneous retrograde access sites in the left and right common femoral arteries. The method also includes inserting a guide sheath with an integrated stabilization wire. The guide sheath includes a radiopaque tip at its distal end configured to be advanced through the contralateral access site.

The method also includes inserting a snare device into an ipsilateral access site. The snare device includes a snare catheter which contains a coaxial snare wire that has a snare loop at the distal end. The method further includes capturing the stabilization wire with the snare device. In some embodiments, capturing the stabilization wire can include positioning and cinching a distal end of the stabilization wire inside the snare loop under fluoroscopic visualization. The method also includes externalizing the stabilization wire at the ipsilateral access site. In some embodiments, externalizing the stabilization wire includes applying a tensile force to the snare device and a push force to the guide sheath. In some embodiments, the stabilization wire is externalized to position the elongate member at or about the ipsilateral access site. The method also includes reversibly anchoring the externalized stabilization wire at the ipsilateral access site.

Additional features and advantages of the disclosure will be set forth in the description that follows, and in part, will be obvious from the description; or can be learned by practice of the principles disclosed herein. The features and advantages of the disclosure can be realized and obtained by means of the instruments and combinations particularly pointed out in the appended claims. These and other features of the disclosure will become fully apparent from the following description and appended claims, or can be learned by the practice of the principles set forth herein.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings.

Figure 1:
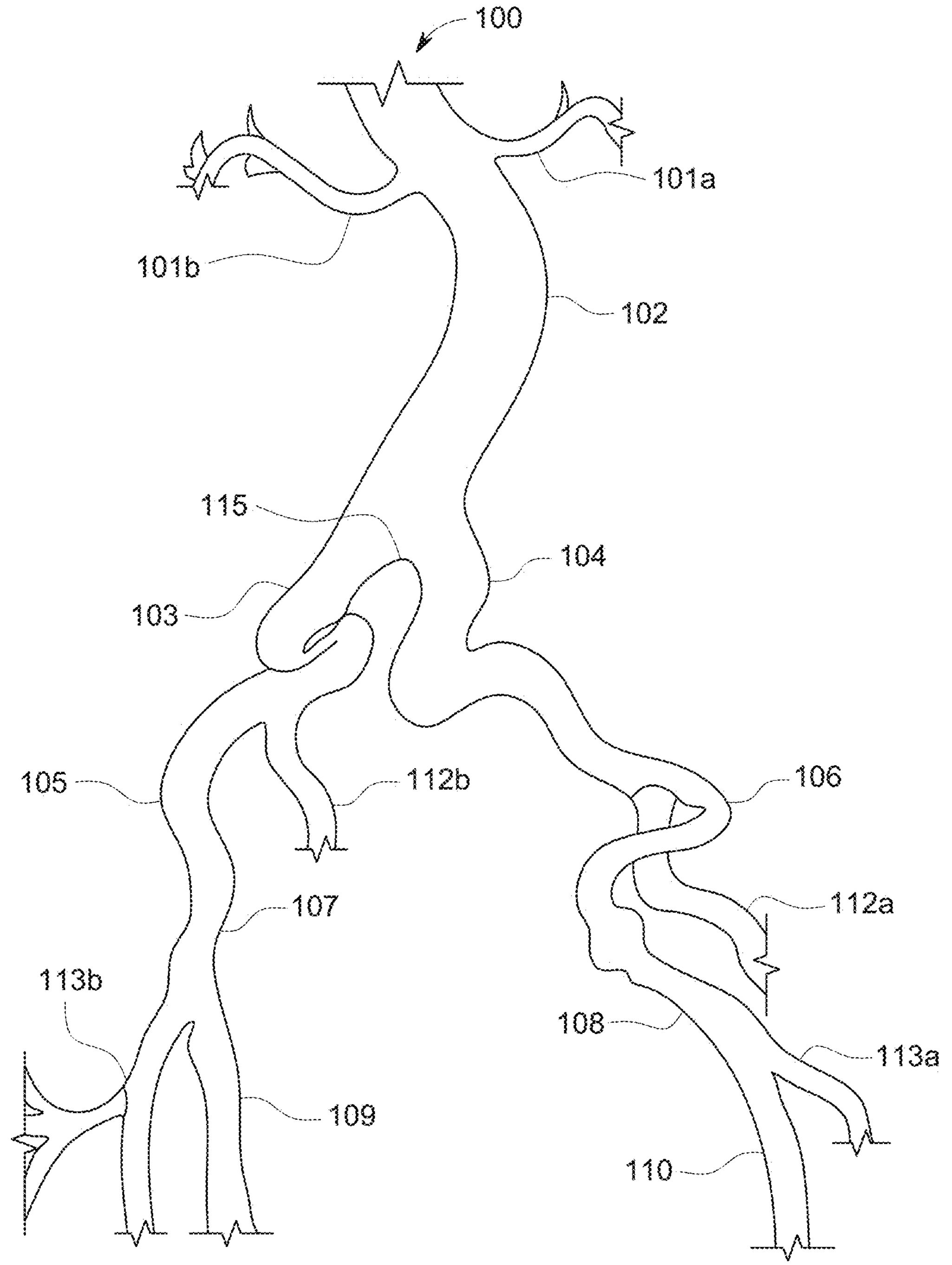
FIG. 1 illustrates an aortic bifurcation and tortuous vessel anatomy, in accordance with an embodiment of this disclosure.

The present disclosure is susceptible to various modifications and alternative forms. Some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF ILLUSTRATED EMBODIMENTS

The present invention is described with reference to the attached figures, where like reference numerals are used throughout the figures to designate similar or equivalent elements. The figures are not drawn to scale, and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present disclosure.

FIG. 1 illustrates an aortic bifurcation and tortuous peripheral artery 100, in accordance with an embodiment of this disclosure. The tortuous peripheral artery 100 can include an abdominal aortic bifurcation with tortuous branch arteries. The tortuous branch arteries can include a right renal artery 101*b* and a left renal artery 101*a* extending from an abdominal aorta 102. The abdominal aorta 102 can be parted at an aortic bifurcation 115, and connected to arteries of the lower limbs. The arteries of the lower limbs can include a right common iliac 103 and a left common iliac 104. The left common iliac 104 can be split into a left external iliac 106 and a left internal iliac 112*a*. The left external iliac 106 can be connected to a left common femoral 108, and further split into a left deep femoral 113*a*, and a left superficial femoral 110. The The right common iliac 103 can be connected to a right external iliac 105. The right external iliac 105 can be connected to a right common femoral 107, which splits into a right deep femoral 113*b* and a right superficial femoral 109. FIG. 1 illustrates the tortuous nature of the peripheral arteries.

When performing interventions within the tortuous peripheral artery 100, it is common to encounter difficulties associated with access and pushability. For example, a highly angulated aortic bifurcation 115 or the extremely tortuous common iliac arteries 103 and 104 can be extremely difficult to traverse. Furthermore, these arteries can contain calcific plaques or other obstructions which can add anatomic and technical challenges when traversing the tortuous peripheral artery 100.

Figure 2:
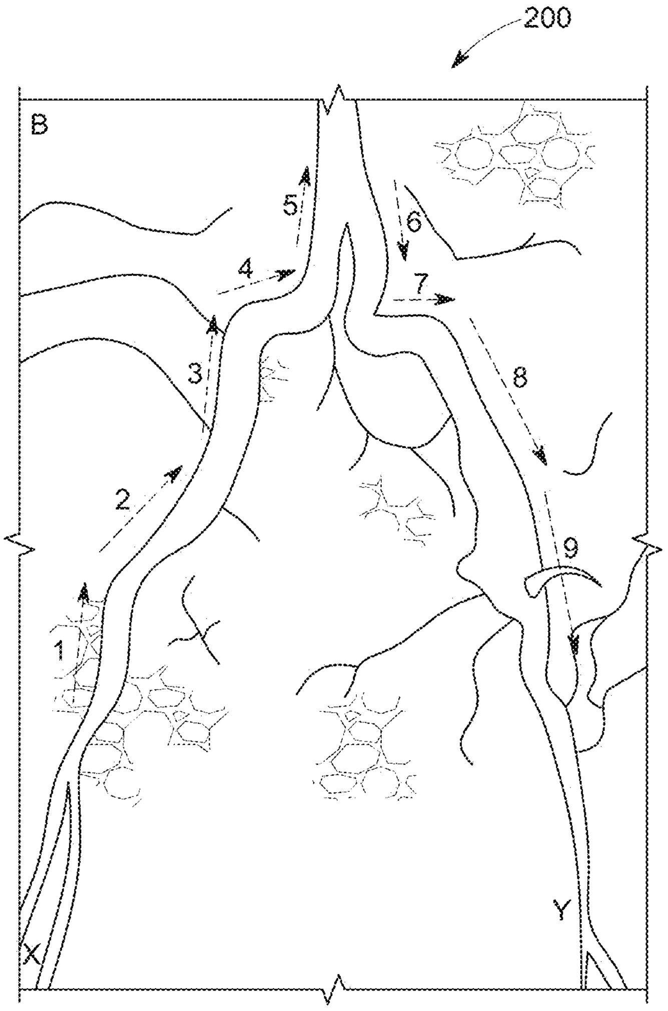
FIG. 2 illustrates a tortuous anatomical pathway from the percutaneous access within the common femoral artery on the contralateral side to a potential procedure location in the artery on the ipsilateral side, in accordance with an embodiment of the disclosure.

FIG. 2 illustrates a tortuous anatomical pathway 200 from the percutaneous access within the common femoral artery on the contralateral side to a potential procedure location on the ipsilateral side, in accordance with an embodiment of the disclosure. In some embodiments, interventional devices such as wires and catheters are pushed from the contralateral access at point 'X' to the treatment site 'Y'. The devices would need to travel through the general pathways 1 through 9. Due to the multi directional twists and turns along the pathways 1 through 9, the devices can suffer from a significant loss of performance such as torque and pushability. While FIG. 2 illustrates the tortuous anatomical pathway 200 in a two-dimensional format, the tortuousity of the anatomical pathway 200 is often significantly more severe, as illustrated in FIG. 1.

Figure 3A:
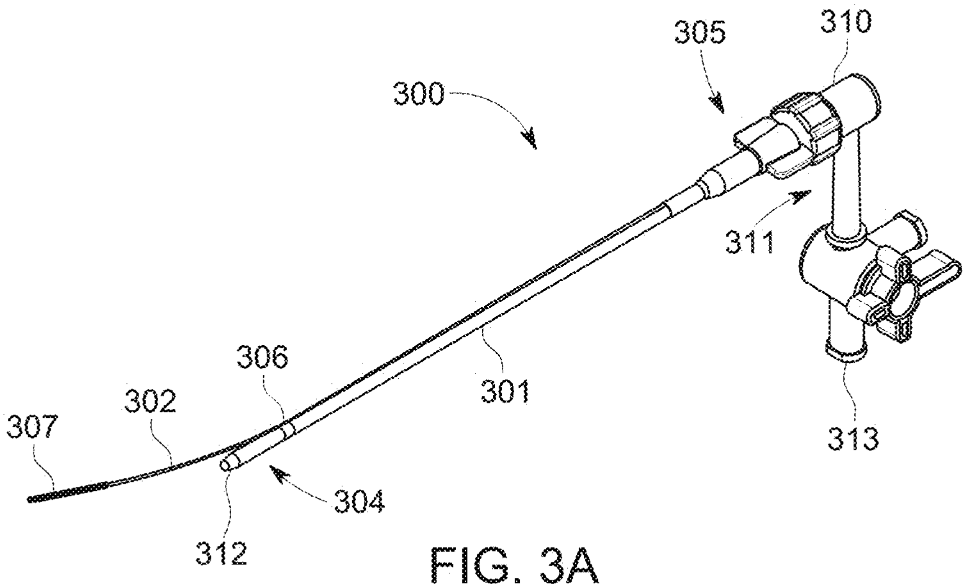
FIG. 3A illustrates a guide sheath with an integrated stabilization wire in accordance with an embodiment of the disclosure.

FIG. 3A illustrates a guide sheath 300 with an integrated stabilization wire 302 in accordance with an embodiment of the disclosure. The guide sheath 300 can include an elongate member 301 with a proximal end 305 and a distal end 304 located opposite of the proximal end 305. The elongate member 301 can be made up of materials commonly known in the art including, for example, metal tubing, reinforced or unreinforced polymeric tubing with or without radiopaque fillers, or combinations thereof. The metal tubing can include stainless steel, nickel titanium, cobalt chromium, copper, aluminum, or the like. The reinforced polymeric tubing can include braid or coil structures or combinations thereof. The reinforced polymeric tubing can be made up of stainless steel, nickel titanium, composites, metal reinforced polymer, polymer, or a combination thereof. The elongate member 301 can further include one or more radiopaque markers along its length, such as distal radiopaque marker 308 and proximal radiopaque marker 309. The radiopaque markers 308 and 309 can be at the distal tip or at the transition point of bifurcation and located between the proximal and distal end of the elongate member 301. Alternatively, the radiopaque markers 308 and 309 can be located between the midpoint and distal end of the elongate member 301.

The distal radiopaque marker 308 can provide visualization of the distal most tip of the elongate member 301 under fluoroscopy. The proximal radiopaque marker 309 can provide the user with a visual guidance as to the exact location of the stabilization wire transition 306 under fluoroscopy to aid in positioning at the ipsilateral access. The radiopaque markers 308 and 309 can be a coil, a tube fabricated using gold, platinum, iridium, barium sulfate loaded polymers, or a combination thereof. The radiopaque markers 308 and 309 can be attached to the elongate member 301 using welding, heat fusing, adhesive bonding, mechanical locking, crimping, laminating, soldering, or the like.

The proximal end 305 can include a hub with hemostasis valve 310 and a side port 311 that may include a stopcock with luer connector 313. The distal end 304 can include a stabilization wire transition 306 connected to the side wall of the elongate member 301. The hub with hemostasis valve 310 can be a valve and hemostatic device such as a touhy borst valve, duck-bill valve, o-ring, or a combination thereof. The hemostasis valve 310 can allow passage of procedural catheters and interventional devices through the lumen 312 of elongate member 301 while maintaining hemostasis. In some embodiments, the stopcock with luer connector 313 facilitates communication with the lumen 312 of the elongate member 301 and facilitates an injection of fluids, such as saline, contrast, $CO_2$ gas or medicines. The stabilization wire 302 bifurcates alongside the elongate member 301 at the stabilization wire transition 306 and extends beyond the distal section of the guide sheath 300. The stabilization wire 302 can include a distal segment 307.

In some embodiments, the stabilization wire 302 can be made up of a solid or hollow member with a cross-section that is round, flat, rectangular, or a combination thereof. The stabilization wire 302 can be fabricated using commonly known materials in the art including, for example, stainless steel, nickel titanium, composites, metal reinforced polymer, polymer, a combination thereof, or the like. The stabilization wire 302 can be attached to the elongate member 301 by methods known in the art including, for example, welding, heat fusing, adhesive bonding, mechanical locking, crimping, laminating, soldering, or the like.

The stabilization wire 302 can be connected to the elongate member 301 by a single point at the stabilization wire transition 306. In alternative embodiments, a proximal segment of the stabilization wire 302 can be embedded within or along at least some portion of an elongate member wall (not shown) within the elongate member 301. In addition, the distal segment 307 of the stabilization wire 302 can be reduced in size to enhance flexibility using methods commonly known in the art including, for example, centerless grinding, necking, drawing, cold working, and the like.

The distal segment 307 of the stabilization wire 302 can be made up of radiopaque material to provide enhanced visualization under fluoroscopic guidance. The radiopaque material can include a coil, a tube or the like. The radiopaque material can be fabricated using materials commonly known in the art including, for example, gold, platinum, iridium, barium sulfate loaded polymers, or a combinations thereof, or the like. The radiopaque material can be attached to the distal segment 307 of the stabilization wire 302 using methods commonly known in the art including, for example, welding, heat fusing, adhesive bonding, mechanical locking, crimping, laminating, soldering, or the like.

Figure 3B:
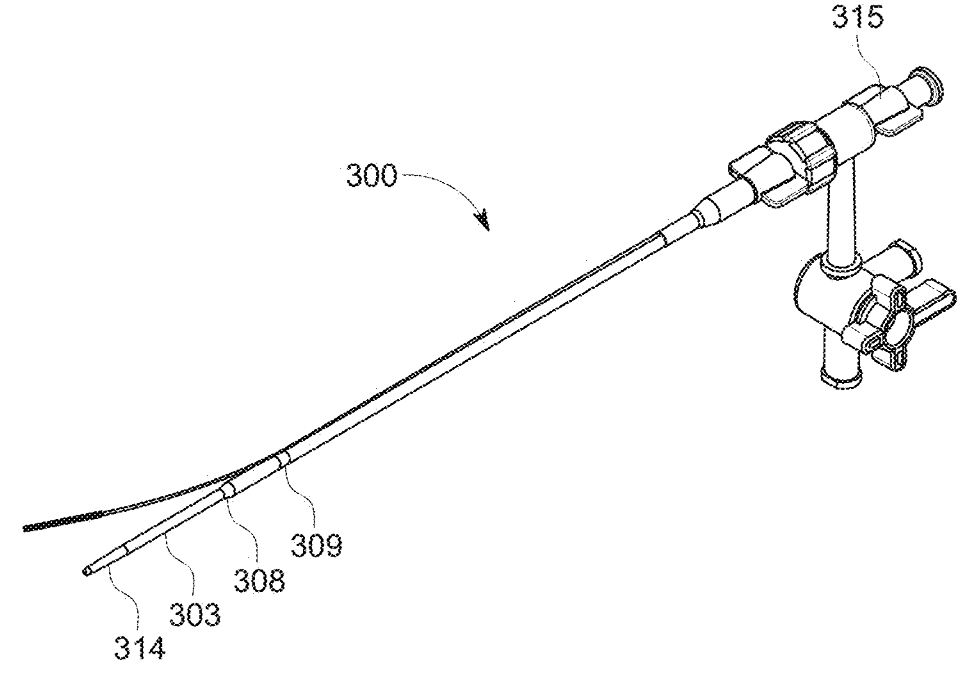
FIG. 3B illustrates a guide sheath of FIG. 3A with the addition of a dilator assembled within the lumen of the guide sheath in accordance with an embodiment of the disclosure.

FIG. 3B illustrates the guide sheath 300 with dilator 303 coaxially assembled within the guide sheath 300. The dilator 303 can include a distal end 314. In some embodiments, the dilator 303 can be assembled within the lumen 312 of the guide sheath 300. The dilator 303 can include a lumen (not shown) disposed along its length sized to facilitate passage of endovascular guide wires. The dilator 303 can be constructed using a rod or tube fabricated using methods and materials such as metallic and polymeric materials with or without radiopaque fillers (e.g. stainless steel, Nitinol, Pebax, high or low density Polyethylene, Nylon, Polypropylene, combinations thereof, or the like). The dilator 303 can be made using fabrication methods such as extrusion, drawing, injection molding, 3-D printing, or combinations thereof. The dilator distal end 314 can incorporate a tapered tip to smoothen the dimensional transition between the elongate member 301 to a guide wire (not shown) that may be disposed within the lumen (not shown) of the dilator 303. The proximal end of the dilator 303 can include a hub 315 that can be reversibly locked to the hub with hemostasis valve 310 of the guide sheath 300 to maintain the position of the dilator 303 relative to the guide sheath 300 during delivery to the target location.

FIGS. 4 to 8 illustrate an exemplary process for endovascular treatment of tortuous aortoiliac arteries implementing the guide sheath 300 with integrated stabilization wire 302, in accordance with an embodiment of the disclosure. Furthermore, FIGS. 4 to 8 illustrate the process of providing end-to-end stability to any procedural catheters and other interventional devices introduced through the procedural lumen 312 of the guide sheath 300.

Figure 4:
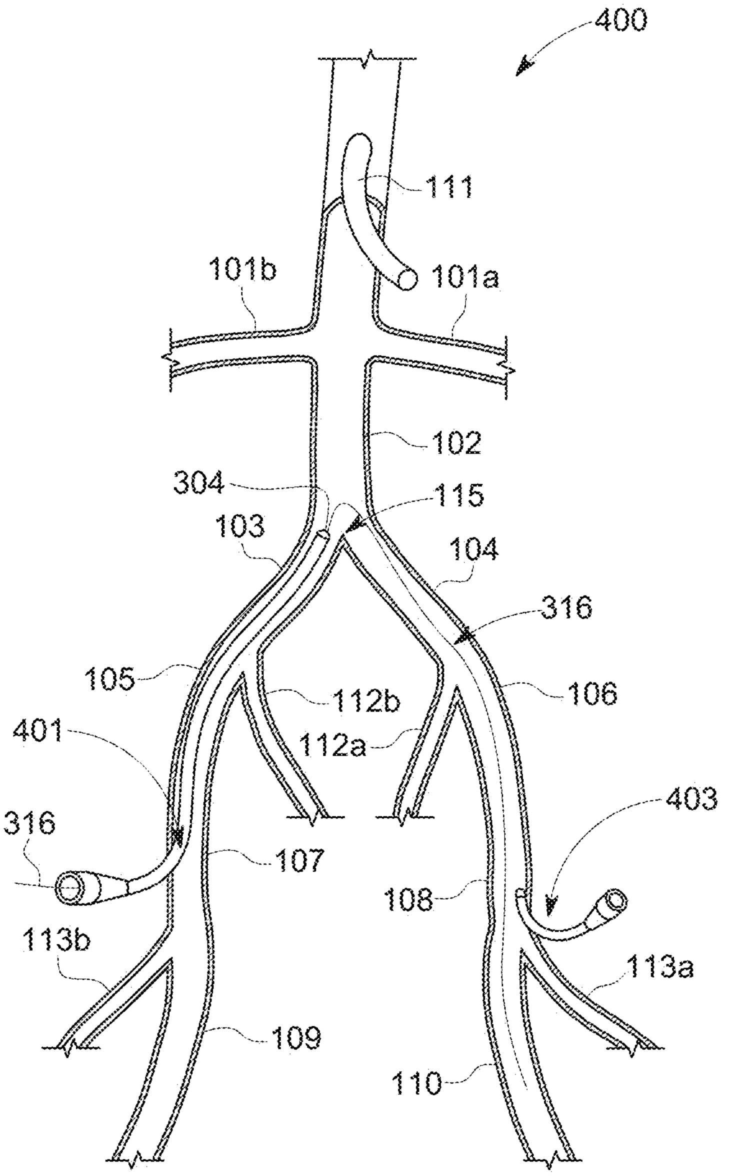
FIG. 4 illustrates a main access sheath placed through a percutaneous, contralateral femoral access, with its tip guided to the aortic bifurcation and a low profile, access sheath placed through a percutaneous, ipsilateral femoral access, in accordance with an embodiment of the disclosure.

FIG. 4 illustrates a diagram 400 where a main access sheath 401 is introduced percutaneously over an access guide wire 316 through the contralateral femoral access site 402 and into the right common femoral artery 107 using standard technique. The main access sheath 401 can include a 7 French vascular introducer sheath. The access guide wire 316 can typically be positioned such that it can gain access to the ipsilateral common femoral artery and/or to the ipsilateral vasculature. The dilator (not shown) of the main access sheath 401 can be loaded and advanced over the access guide wire 316 towards the right external iliac artery 105 and right common iliac artery 103 until the tip of main access sheath 401 reaches the aortic bifurcation 115.

Once the tip of main access sheath 401 reaches the aortic bifurcation 115, the main access sheath dilator (not shown) is removed while the main access sheath 401 and the access guide wire 316 are left in place. The main access sheath 401 can be positioned under fluoroscopic guidance with the aid of radiopaque tip marker 405. FIG. 4 also illustrates the percutaneous introduction of a low profile, ipsilateral femoral access sheath 403 through access site 404 to introduce a snare device (not shown) into the left common femoral artery 108 on the ipsilateral side. The ipsilateral femoral access sheath 403 can include a 4 French vascular introducer sheath.

Figure 5:
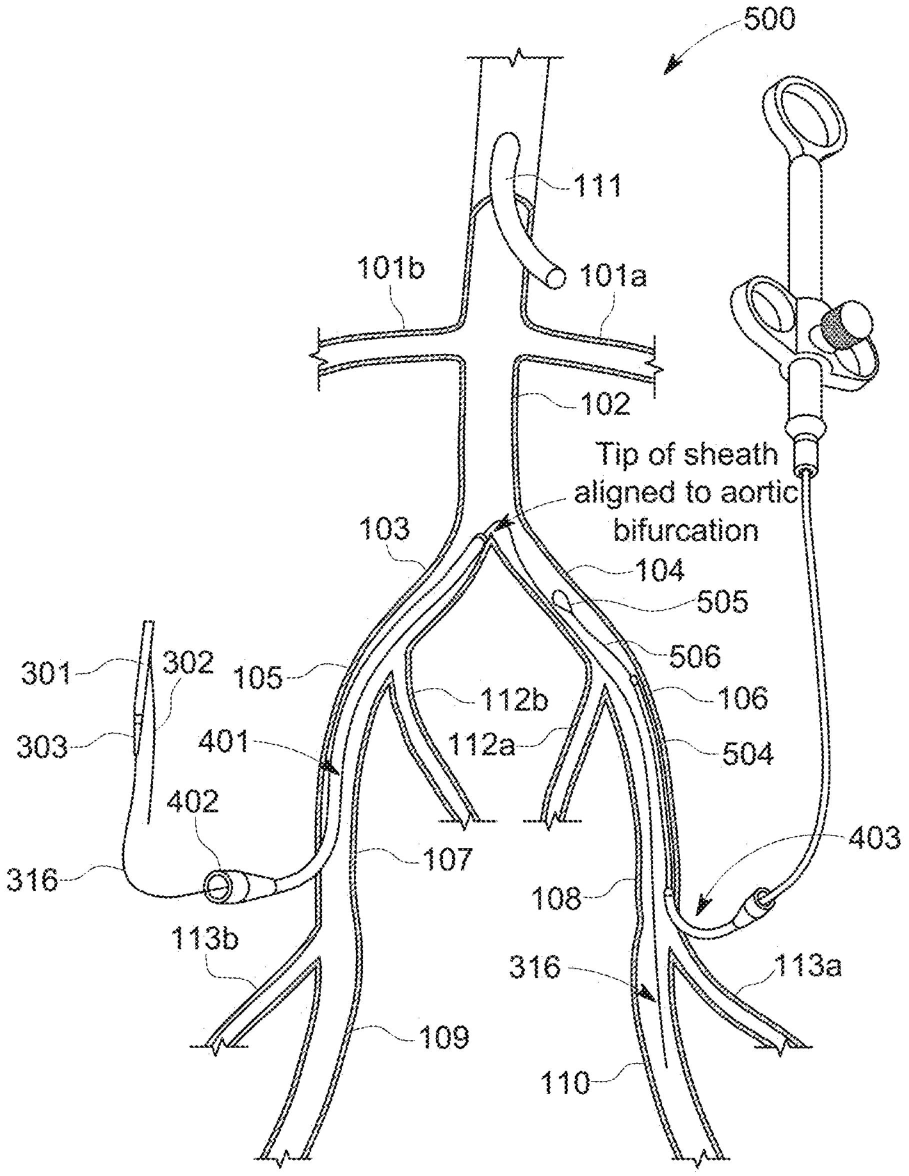
FIG. 5 illustrates a process of inserting a snare device into the main access sheath of FIG. 4 and advancing the snare device to the aortic bifurcation through the ipsilateral access, in accordance with an embodiment of the disclosure.

FIG. 5 illustrates a process of inserting a snare device 504 into the ipsilateral femoral access sheath 403 and advancing the snare catheter 504 to the aortic bifurcation through the ipsilateral access. The snare catheter 504 can include a snare wire 506 introduced through the ipsilateral femoral access sheath 403. The snare wire 506 can include a 20 to 30 mm (or smaller) snare loop 505 at its distal end. The snare catheter 504 can be advanced towards the aortic bifurcation 115 to position the snare loop 505 in the abdominal aorta to accept and capture the stabilization wire 302. The dilator 303 of guide sheath 300 can be loaded over the access guide wire 316 and positioned close to the proximal hub 402 of the main access sheath 401.

Figure 6:
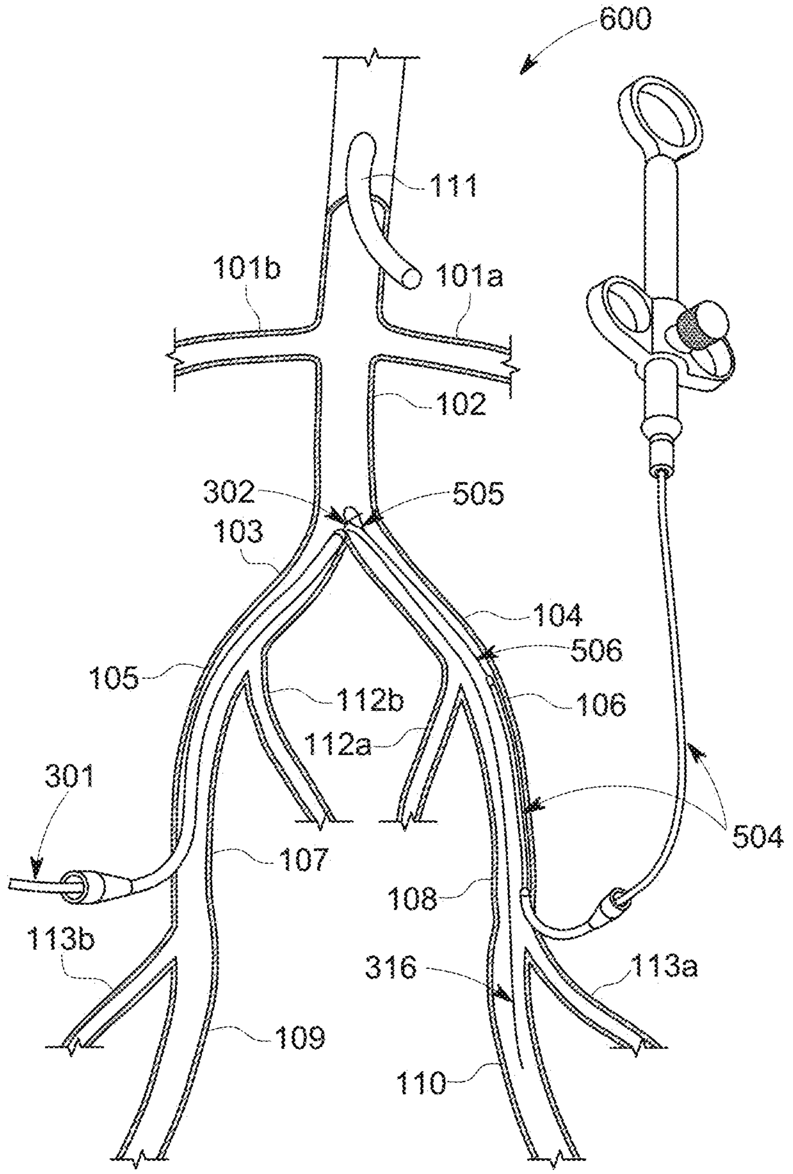
FIG. 6 illustrates a process of inserting the guide sheath of FIG. 3A through the main access sheath of FIG. 4 to the aortic bifurcation and snaring of the stabilization wire, in accordance with an embodiment of the disclosure.

FIG. 6 illustrates a process of inserting the guide sheath 300 (of FIG. 3A) through the main access sheath 401 (of FIG. 4), in accordance with an embodiment of the disclosure. The guide sheath 300 can include an integrated stabilization wire 302 exposed at or about the distal tip of the main access sheath 401. In some embodiments, the integrated stabilization wire 302 of guide sheath 300 is first introduced into main access sheath 401 with the aid of a guide wire introducer (not shown) and advanced alongside the pre-positioned main access guide wire 316 towards the aortic bifurcation 115. The tip of the integrated stabilization wire 302 can be finally positioned inside the snare loop 505. The stabilization wire 302 can then be captured and secured by the snare loop 505 by advancing the snare catheter 504 until the snare loop 505 collapses into the lumen of the snare catheter 504.

Figure 7:
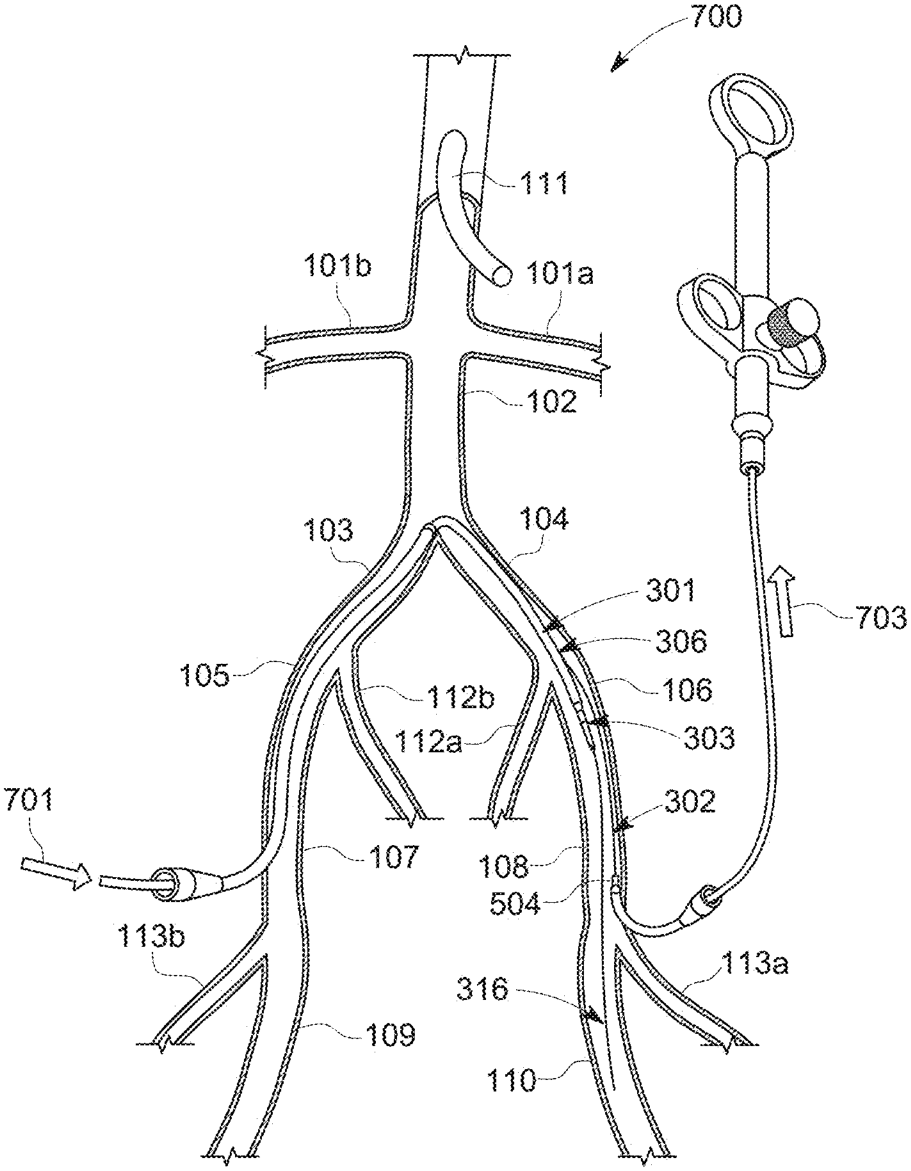
FIG. 7 illustrates a process of applying a pull force to the guide sheath of FIG. 3A into the ipsilateral iliac artery by retracting the snare device while providing a push force on the guide sheath from the contralateral side to externalize the stabilization wire, in accordance with an embodiment of the disclosure.

FIG. 7 illustrates a process of applying a pull force 703 to the guide sheath 300 by retracting the snare catheter 504 while providing a push force 701 on the guide sheath 300 (not labeled) from the contralateral side to externalize the stabilization wire 302. The pull force 703 can be applied to the distal end of the guide sheath 300 (not labeled). Of note, 301 which is the elongate member of the guide sheath is labeled. This pull force 703 is derived from the operator's retraction of the snare catheter 504 which has securely captured the stabilization wire 302. Simultaneously, a push force 701 can be applied to the proximal end of the guide sheath 300 (not labeled). These push and pull forces enable the guidance and ease placement of sheath 300 (not labeled), over the aortic bifurcation 115 and down the ipsilateral left iliac artery 104. The guide sheath 300 (not labeled) with the dilator 303 and the stabilization wire 302 can be guided to the left common femoral artery access site 404 (as shown in FIG. 4). The stabilization wire 302 can be externalized (i.e. out of the patient's body) [not shown] by retracting it through the low profile ipsilateral access sheath 403 (labeled previously in FIGS. 4 and 5). The stabilization wire 302 may be retracted (not shown in FIG. 7, but shown in FIG. 8) until the stabilization wire transition 306 is positioned at or about the distal tip of the low profile ipsilateral sheath 403.

Figure 8:
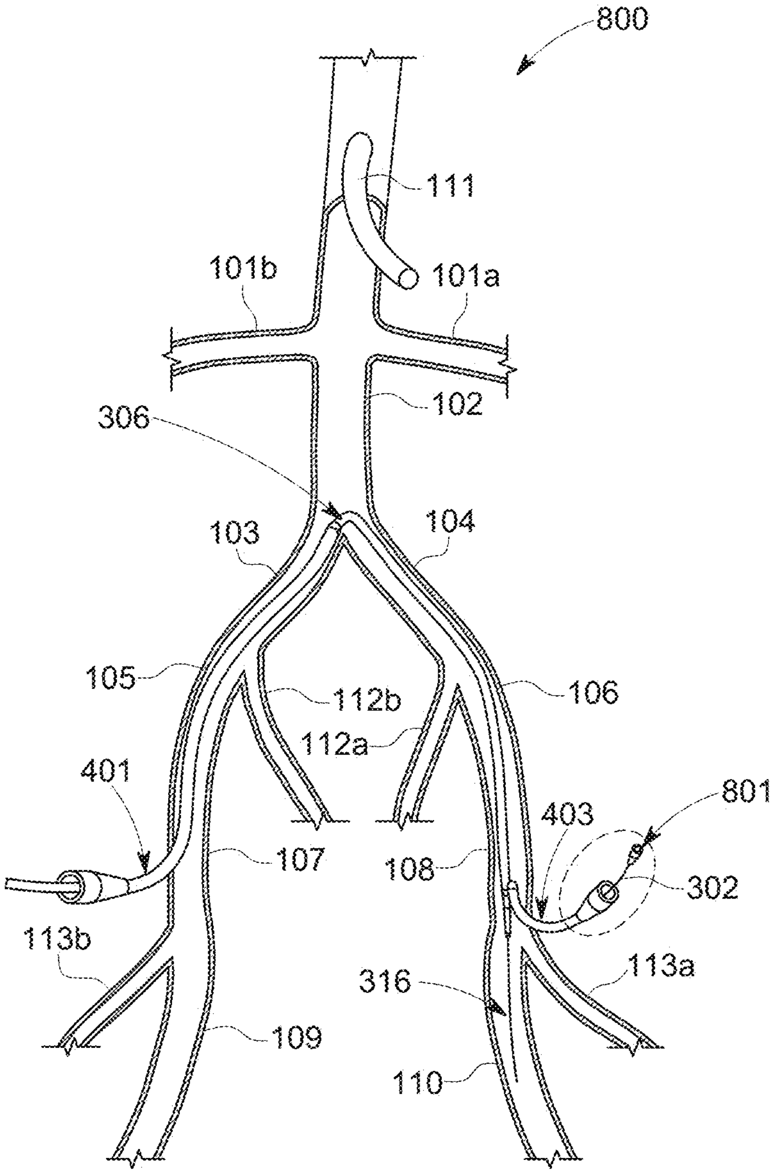
FIG. 8 illustrates a process of anchoring an externalized stabilization wire of the guide sheath of FIG. 3A to provide end-to-end stabilization for the procedural lumen, in accordance with an embodiment of the disclosure.

FIG. 8 illustrates a process of anchoring an externalized stabilization wire 302 of the guide sheath 300 (not labeled) to provide end-to-end stabilization for the procedural lumen. The stabilization wire 302 can be anchored in place by sliding a torque device 801 (or using any equivalent locking device) over the externalized portion of the stabilization wire 302. The stabilization wire 302 can then be tightened or otherwise locked or anchored at or about the hub of the low profile ipsilateral access sheath 403. By locking or anchoring the stabilization wire 302 outside the low profile ipsilateral access sheath 403, the guide sheath 300 (not labeled) is securely stabilized and tethered. In this way, the guide sheath 300 (not labeled) is prevented from backing up and/or prolapsing into the abdominal aorta 102 when advancing procedural catheters and other interventional devices through the main lumen of guide sheath 300 (not labeled). Ultimately, the anchored guide sheath 300 (not labeled) provides superior pushability of interventional devices, thereby allowing more distal access to the ipsilateral limb vessels and enabling crossing of tight lesions or even chronic total occlusions. Furthermore, this enhanced stability enables the use of stiffer devices (e.g. atherectomy catheters), which typically may elicit prolapse of a guide sheath that is not anchored.

Figure 9:
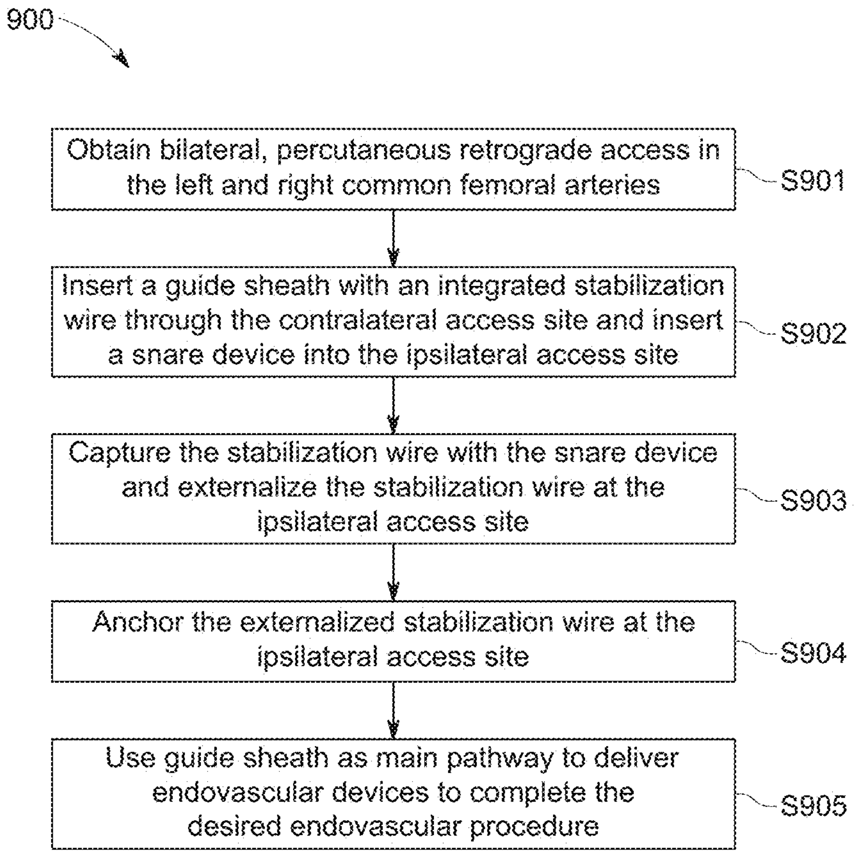
FIG. 9 illustrates a process flow diagram for accessing and stabilizing the guide sheath in lower limb interventions, in accordance with an exemplary embodiment of the disclosure.

FIG. 9 provides a flow chart diagram 900 for accessing and stabilizing the guide sheath 300 with an integrated stabilization wire 302 in lower limb interventions, indicated by general reference character 900. The process commences at step S901 where the bilateral, percutaneous retrograde access is obtained for the left and right common femoral arteries.

At step S902, a guide sheath is inserted with an integrated stabilization wire through the contralateral access site and the snare device is inserted into the ipsilateral access site. At step S903, the stabilization wire is captured with the snare device and the stabilization wire at the ipsilateral access site is externalized. At step S904, the externalized stabilization wire anchored at the ipsilateral access site. Finally, the process advances to S905, where the guide sheath is used as a main pathway to deliver endovascular devices to complete the desired endovascular procedure.

While the stabilization schemes proposed above describe a guide sheath with integrated stabilization wire that can provide stability in procedures conducted in tortuous branches of major peripheral vessels of the lower extremities, it is understood that it is not meant to be exhaustive. There may be other scenarios possible for access and stabilization of procedural catheter or sheath depending on the location of the procedure and the nature of the patient such as radial or brachial access. The preferred method will vary based on the location of the procedure and the nature of the patient.

What is claimed is:

1. An apparatus enabled to perform a lower extremity vasculature procedure comprising:

a sheath catheter, the sheath catheter comprising a catheter body comprising a proximal end and a distal end and a lumen therein; and a stabilization wire partially integrated and attached to a wall of the catheter body within the lumen of the sheath catheter between the proximal and distal ends, and the stabilization wire extending beyond the distal end of the catheter body;

wherein a distal end of the stabilization wire and the distal end of the sheath catheter are insertable into lower extremity vasculature via a contralateral percutaneous access;

wherein the distal end of the stabilization wire and the distal end of the sheath catheter are guidable from the contralateral percutaneous access to exit the lower extremity vasculature at an ipsilateral percutaneous access; and wherein the apparatus is capable of applying a tension and a stabilization to the sheath catheter via the distal end of the stabilization wire outside the ipsilateral percutaneous access and the proximal end of the sheath catheter outside the contralateral percutaneous access.

2. The apparatus of claim 1, wherein the distal end of the sheath catheter with the distal end of the stabilization wire extending beyond the distal end of the catheter body are configured to be inserted into the vasculature via contralateral percutaneous access and guided within the vasculature to the ipsilateral percutaneous access using a plurality of radio-opaque markers affixed to the catheter body.

3. The apparatus of claim 2, wherein a proximal end of the sheath catheter is connected to a hub configured to be outside the contralateral percutaneous access;

wherein the hub is enabled to fix the proximal end of the sheath catheter outside the contralateral percutaneous access while providing guidance capability within the vasculature to the sheath catheter; and the hub is also enabled to provide hemostasis at the contralateral percutaneous access.

4. The apparatus of claim 1, wherein the stabilization wire has a flat cross section where the stabilization wire is attached to the wall of the catheter body within the lumen and a circular cross section where the stabilization wire extends beyond the distal end of the catheter body.

5. A system for enabling a performing of a lower extremity vasculature procedure, the system comprising:

a sheath catheter comprising a catheter body having a proximal end and a distal end and a lumen therein between;

the sheath catheter comprising a stabilization wire partially integrated and attached to a wall of the catheter body within the lumen between the proximal end and the distal ends of the sheath catheter;

the distal end of the stabilization wire extending beyond the distal end of the sheath catheter;

the distal end of the sheath catheter with the distal end of the stabilization wire configured to be inserted via a contralateral percutaneous access and guided through vasculature to an ipsilateral percutaneous access close to a procedural site within the lower extremity vasculature using radio-opaque markers on the catheter body;

the proximal end of the sheath catheter attached to a hub configured to be outside the contralateral percutaneous access, the hub enabled to provide a guidance capability within the vasculature for the sheath catheter and a hemostasis at the contralateral percutaneous access;

the distal end of the stabilization wire is configured to exit the vasculature at the ipsilateral percutaneous access;

wherein the system is configured to apply a tension and stabilization to the sheath catheter via the distal end of the stabilization wire outside the ipsilateral percutaneous access and the proximal end of the sheath catheter outside the contralateral percutaneous site; and wherein the application of the tension and stabilization applied to the sheath catheter enable for the system to provide a stabilized access to a procedural site for procedural catheters and instruments inserted through the sheath catheter for performing the lower extremity vasculature procedure.

6. The system of claim 5, wherein the stabilization wire has a rectangular cross section within the body of the sheath catheter and a round cross section outside the body of the sheath catheter.

7. The system of claim 5, wherein a stabilized access provided to procedural catheters and instruments enable an ease of access to the procedural site and a reduction of a time of the lower extremity vasculature procedure.

8. An apparatus enabled to perform a lower extremity vasculature procedure comprising:

a sheath catheter, the sheath catheter comprising a catheter body comprising a proximal end and a distal end and a lumen therein; and a stabilization wire partially integrated and attached to a wall of the catheter body within the lumen of the sheath catheter between the proximal and distal ends, and the stabilization wire extending beyond the distal end of the catheter body;

wherein the distal end of the sheath catheter with the distal end of the stabilization wire extending beyond the distal end of the catheter body are configured to be inserted into the vasculature via contralateral percutaneous access and guided within the vasculature to the ipsilateral percutaneous access using a plurality of radio-opaque markers affixed to the catheter body;

wherein a proximal end of the sheath catheter is connected to a hub configured to be outside the contralateral percutaneous access;

wherein the hub is enabled to fix the proximal end of the sheath catheter outside the contralateral percutaneous access while providing guidance capability within the vasculature to the sheath catheter; and wherein the hub is also enabled to provide hemostasis at the contralateral percutaneous access.

9. The apparatus of claim 8, wherein a distal end of the stabilization wire is configured to exit the vasculature and be outside an ipsilateral percutaneous access.

10. The apparatus of claim 9, wherein having the proximal end of the sheath catheter outside the contralateral percutaneous access and the distal end of the stabilization wire outside the ipsilateral percutaneous access enable application of a tension between the proximal end and the distal end of the sheath catheter.

11. The apparatus of claim 10, wherein the application of a tension between the proximal end and the distal end of the sheath catheter enable the sheath catheter to provide a support and a stability to a procedural catheter inserted into the vasculature via the sheath catheter.

12. An apparatus enabled to perform a lower extremity vasculature procedure comprising:

a sheath catheter, the sheath catheter comprising a catheter body comprising a proximal end and a distal end and a lumen therein; and a stabilization wire partially integrated and attached to a wall of the catheter body within the lumen of the sheath catheter between the proximal and distal ends, and the stabilization wire extending beyond the distal end of the catheter body;

wherein the distal end of the sheath catheter with the distal end of the stabilization wire extending beyond the distal end of the catheter body are configured to be inserted into the vasculature via contralateral percutaneous access and guided within the vasculature to the ipsilateral percutaneous access using a plurality of radio-opaque markers affixed to the catheter body; and wherein the stabilization wire has a flat cross section where the stabilization wire is attached to the wall of the catheter body within the lumen and a circular cross section where the stabilization wire extends beyond the distal end of the catheter body.

* * * * *